(12) United States Patent
Bedard et al.

(10) Patent No.: US 8,883,194 B2
(45) Date of Patent: *Nov. 11, 2014

(54) ADSORBENT-CONTAINING HEMOSTATIC DEVICES

(75) Inventors: Robert L. Bedard, McHenry, IL (US); Steven A. Wilcher, Glencoe, IL (US)

(73) Assignee: Honeywell International, Inc., Morristown, NJ (US)

( * ) Notice: Subject to any disclaimer, the term of this patent is extended or adjusted under 35 U.S.C. 154(b) by 45 days.

This patent is subject to a terminal disclaimer.

(21) Appl. No.: 11/937,527

(22) Filed: Nov. 9, 2007

(65) Prior Publication Data

US 2009/0123525 A1  May 14, 2009

(51) Int. Cl.
| | |
|---|---|
| A61F 13/00 | (2006.01) |
| A61L 15/18 | (2006.01) |
| A61L 15/24 | (2006.01) |
| A61K 31/785 | (2006.01) |
| A61K 33/06 | (2006.01) |
| A61K 45/06 | (2006.01) |
| A61L 15/42 | (2006.01) |

(52) U.S. Cl.
CPC ............ *A61K 33/06* (2013.01); *A61L 2400/04* (2013.01); *A61L 15/18* (2013.01); *A61K 45/06* (2013.01); *A61F 2013/00463* (2013.01); *A61L 15/425* (2013.01); *A61L 15/24* (2013.01)
USPC .................. 424/443; 424/447; 424/78.35

(58) Field of Classification Search
None
See application file for complete search history.

(56) References Cited

U.S. PATENT DOCUMENTS

| | | | | |
|---|---|---|---|---|
| 3,628,534 | A | * 12/1971 | Donohue | 604/366 |
| 3,993,640 | A | * 11/1976 | Pickard et al. | 536/30 |
| 4,051,848 | A | 10/1977 | Levine | |
| 4,104,226 | A | * 8/1978 | Melzer et al. | 524/516 |
| 4,282,059 | A | * 8/1981 | Davidson | 162/158 |
| 4,454,055 | A | * 6/1984 | Richman et al. | 252/194 |
| 4,469,746 | A | 9/1984 | Weisman et al. | |
| 4,525,410 | A | 6/1985 | Hagiwara et al. | 428/198 |
| 4,775,585 | A | 10/1988 | Hagiwara et al. | 428/323 |
| 4,822,349 | A | 4/1989 | Hursey et al. | 604/367 |
| 4,826,497 | A | 5/1989 | Marcus et al. | 604/359 |
| 4,911,898 | A | 3/1990 | Hagiwara et al. | 423/118 |
| 4,938,958 | A | 7/1990 | Niira et al. | 424/79 |
| 4,959,268 | A | 9/1990 | Hagiwara et al. | 428/403 |
| 5,064,599 | A | 11/1991 | Ando et al. | 264/237 |
| 5,084,427 | A | 1/1992 | Tsoucalas | 502/62 |
| 5,120,693 | A | 6/1992 | Connolly et al. | 502/64 |
| 5,470,585 | A | 11/1995 | Gilchrist | 424/604 |
| 5,489,469 | A | 2/1996 | Kobayashi et al. | 428/283 |
| 5,503,908 | A | 4/1996 | Faass | 428/198 |
| 5,556,699 | A | 9/1996 | Niira et al. | 428/323 |
| 5,614,570 | A | 3/1997 | Hansen et al. | 524/13 |
| 5,643,589 | A | 7/1997 | Chalmers | 424/404 |
| 5,650,221 | A | 7/1997 | Belding et al. | |
| 5,744,404 | A | 4/1998 | Titterton et al. | 442/63 |
| 5,800,372 | A | 9/1998 | Bell et al. | 602/48 |
| 5,874,164 | A | * 2/1999 | Caldwell | 428/306.6 |
| 5,981,052 | A | 11/1999 | Sugiyama | 428/311.71 |
| 6,060,461 | A | 5/2000 | Drake | 514/54 |
| 6,102,107 | A | 8/2000 | Dunne | |
| 6,123,925 | A | 9/2000 | Barry et al. | 424/49 |
| 6,187,347 | B1 | 2/2001 | Patterson et al. | 424/646 |
| 6,229,062 | B1 | * 5/2001 | Mandell et al. | 604/367 |
| 6,277,772 | B1 | 8/2001 | Gancet et al. | 442/327 |
| 6,441,265 | B1 | 8/2002 | Chan | 602/53 |
| 6,472,162 | B1 | 10/2002 | Coelho et al. | 435/13 |
| 6,486,378 | B1 | 11/2002 | Areskoug et al. | |
| 6,495,367 | B1 | 12/2002 | Isogawa et al. | 436/18 |
| 6,521,265 | B1 | 2/2003 | Patterson | 424/646 |
| 6,592,888 | B1 | 7/2003 | Jensen et al. | 424/443 |
| 6,632,678 | B2 | 10/2003 | Aiken et al. | 436/69 |
| 6,638,296 | B2 | 10/2003 | Levinson | 606/213 |
| 6,700,032 | B1 | 3/2004 | Gray | |
| 6,712,934 | B2 | * 3/2004 | Ahlgren et al. | 162/181.6 |
| 6,750,261 | B1 | 6/2004 | Clear et al. | |
| 6,790,429 | B2 | 9/2004 | Ciampi | 423/594.1 |
| 6,890,342 | B2 | 5/2005 | Zhu et al. | 606/213 |
| 6,890,344 | B2 | 5/2005 | Levinson | 606/213 |
| 6,974,562 | B2 | 12/2005 | Ciampi et al. | 422/199 |
| 6,991,802 | B1 | 1/2006 | Ahola et al. | |
| 6,992,233 | B2 | 1/2006 | Drake et al. | 602/48 |
| 6,998,510 | B2 | 2/2006 | Buckman et al. | 602/48 |
| 7,019,191 | B2 | 3/2006 | Looney et al. | |
| 7,056,722 | B1 | 6/2006 | Coelho et al. | 435/214 |
| 7,074,981 | B2 | 7/2006 | Chalmers | 602/41 |
| 7,252,837 | B2 | 8/2007 | Guo et al. | |

(Continued)

FOREIGN PATENT DOCUMENTS

| | | |
|---|---|---|
| EP | 0389015 A2 | 2/1990 |
| EP | 0888783 A1 | 6/1998 |

(Continued)

OTHER PUBLICATIONS

Xiao et al. Cationic-modified cyclodextrin nanosphere/anionic polymer as flocculation/sorption systems. Journal of Colloid and Interface Sciences 283 (2005) 406-413.*

(Continued)

*Primary Examiner* — Daniel Sullivan
*Assistant Examiner* — Peter Anthopolos

(57) ABSTRACT

The present invention utilizes a combination of a porous carrier and an adsorbent such as a molecular sieve to make a more effective hemostatic device to treat wounds in mammalian animals. These hemostatic devices contain additives that do not inhibit hemostasis.

21 Claims, No Drawings

(56) References Cited

U.S. PATENT DOCUMENTS

| | | |
|---|---|---|
| 2001/0009831 A1 | 7/2001 | Schink et al. ............ 442/123 |
| 2002/0015726 A1* | 2/2002 | Scamilla Aledo et al. .... 424/446 |
| 2003/0091641 A1 | 5/2003 | Tiller et al. |
| 2003/0133990 A1 | 7/2003 | Hursey et al. ............ 424/601 |
| 2003/0176827 A1 | 9/2003 | Chandra et al. |
| 2003/0208150 A1 | 11/2003 | Bruder et al. ............ 602/48 |
| 2003/0224056 A1 | 12/2003 | Kotha et al. |
| 2004/0116018 A1 | 6/2004 | Fenwick et al. ............ 442/164 |
| 2005/0058721 A1 | 3/2005 | Hursey ............ 424/618 |
| 2005/0074505 A1 | 4/2005 | Hursey ............ 424/682 |
| 2005/0226916 A1 | 10/2005 | Cochrum et al. ............ 424/445 |
| 2006/0014030 A1 | 1/2006 | Langen et al. |
| 2006/0039994 A1 | 2/2006 | Davis ............ 424/601 |
| 2006/0078628 A1 | 4/2006 | Koman et al. ............ 424/672 |
| 2006/0141060 A1 | 6/2006 | Hursey et al. ............ 424/684 |
| 2006/0155235 A1 | 7/2006 | Sawyer ............ 602/48 |
| 2006/0178609 A1 | 8/2006 | Horn et al. ............ 602/48 |
| 2006/0211965 A1 | 9/2006 | Horn et al. ............ 602/13 |
| 2006/0211971 A1 | 9/2006 | Horn et al. ............ 602/41 |
| 2007/0104768 A1 | 5/2007 | Huey et al. |
| 2007/0154509 A1* | 7/2007 | Wilcher et al. ............ 424/422 |
| 2007/0154510 A1* | 7/2007 | Wilcher et al. ............ 424/422 |
| 2007/0160653 A1 | 7/2007 | Fischer et al. |
| 2007/0207186 A1 | 9/2007 | Scanlon et al. |
| 2007/0275073 A1 | 11/2007 | Huey et al. |
| 2009/0155342 A1 | 6/2009 | Diegelmann et al. |

FOREIGN PATENT DOCUMENTS

| | | |
|---|---|---|
| EP | 1 738 779 A1 | 1/2007 |
| EP | 1 797 850 A1 | 6/2007 |
| EP | 1 810 697 A2 | 7/2007 |
| GB | 2259858 A | 8/1991 |
| JP | 57077623 | 5/1982 |
| JP | 60-195452 A | 10/1985 |
| JP | 61145120 | 7/1986 |
| JP | 62153215 | 7/1987 |
| JP | 3026254 | 2/1991 |
| JP | 1992-146218 | 5/1992 |
| JP | 4144565 | 5/1992 |
| JP | 7112021 | 5/1995 |
| JP | 8105885 | 4/1996 |
| JP | 8294527 | 12/1996 |
| JP | 2001-322926 A | 11/2001 |
| JP | 2007144154 | 6/2007 |
| JP | 2008531498 | 8/2008 |
| KR | 20040002799 | 1/2004 |
| WO | WO 93/01819 | 6/1992 |
| WO | WO 01/64148 A1 | 9/2001 |
| WO | WO 02/30479 A1 | 4/2002 |
| WO | WO 0230479 * | 4/2002 |
| WO | WO 2005/027808 A1 | 3/2005 |
| WO | WO 2006/071748 A2 | 7/2006 |
| WO | WO 2006/088912 A2 | 8/2006 |
| WO | WO 2006082188 A1 * | 8/2006 |
| WO | WO 2007024974 A2 * | 3/2007 |
| WO | WO 2007/081996 A2 | 7/2007 |
| WO | 2012007363 A1 | 1/2012 |

OTHER PUBLICATIONS

CAS Registry No. 386707-08-0 (Jan. 25, 2002).*

XP 002674712, Database WPI, Week 200220, Thomson Scientific, London, GB; AN 2002-151557, & JP 2001 322926 A, Nov. 20, 2001; Abstract.

XP002674713, Database WPI, Week 198546, Thomson Scientific, London, GB; AN 1985-286304, & JP 60 195452, Oct. 3, 1985; Abstract.

* cited by examiner

ADSORBENT-CONTAINING HEMOSTATIC DEVICES

BACKGROUND OF THE INVENTION

This invention relates generally to the use of adsorbents to stop bleeding. More particularly, this invention relates to adsorbents incorporated into adsorbent media such as non-woven materials or films that have improved formulations over the prior art. These formulations contain a sufficient amount of these adsorbents to stop blood loss without containing other ingredients that may counteract the hemostatic function of the adsorbents.

Wounds are generally classified as acute or chronic in accordance with their healing tendencies. Acute wounds from trauma or surgery include wounds such as active bleeding wound sites, e.g., wounds that have detectable, unclotted blood. The rapid control of topical bleeding at active bleeding wound sites is of critical importance in wound management, especially for the management of trauma, e.g., as a result of military exercises or surgery.

Conventional approaches such as manual pressure, cauterization, or sutures may be time consuming and are not always effective in controlling bleeding. Trauma care has received great attention recently as United States troops on a daily basis face combat situations that result in wounds accompanied by significant blood loss. In many cases, the individual may have been able to survive the initial injury only to die of blood loss. Given the central role of hemostasis in trauma care, a great deal of attention has been focused on developing products that can rapidly induce clotting, stop the bleeding, form a tight bond to the wound surface, facilitate scab formation and be compatible with the host tissue. Currently there are several categories of products being used that can be differentiated by their mechanism of action. The first category includes materials that accelerate the coagulation process by absorbing water from the blood. The products in this category include basic cotton gauze. Also within this category are products from Johnson & Johnson's Ethicon division that sells its Surgicel™ regenerated cellulose product line in various forms. There are other cellulosic type products in the marketplace. The second category of products seeks to enhance coagulation by adding features that can increase clotting enzymatic activity. Such products may include such components as thrombin, fibrinogen, propyl gallate, aluminum sulfate, fully acetylated glucosamine and ε-aminocaproic acid. Other hemostatic agents have difficulty adhering to wet tissue and lack a framework onto which a clot can adhere.

Each of these prior art products are deficient in at least one aspect. Products that function solely through absorption of water from the blood tend not to be particularly selective in concentrating the blood constituents useful in clotting such as platelets, erythrocytes and plasmas and therefore are not as effective as other products in enhancing coagulation. The second category of products enhance coagulation by adding components such as thrombin, fibrinogen, propyl gallate, aluminum sulfate, fully acetylated glucosamine and ε-aminocaproic acid that increase clotting enzymatic activity. While these products can be very effective at stopping bleeding they can also be quite expensive, have shelf life limitations and in some cases where the components are derived from animals or humans may offer a mechanism for pathogen transfer or allergic reaction. In the third product category, the HemCon product suffers from potential allergenic side effects, short shelf life and high cost. Some of Z-Medica's QuikClot products suffer from problems with high heat of adsorption that can cause significant discomfort to users and limits its utility in heat sensitive parts of the body. One of the QuikClot products is not optimal since it is literally poured onto the wound and must then be carefully washed from the injury. In addition, it has been found that some formulations of prior art products contain one or more ingredients that have a potentially adverse effect upon the product's overall hemostatic ability and when tested individually may in fact encourage bleeding.

A hemostatic material that is biocompatible, provides superior hemostasis, and that can be fabricated into a variety of forms suitable for use in controlling bleeding from a variety of wounds is still sought. This type of hemostatic material is sought for both surgical applications as well as in field treatment of traumatic injuries. In vascular surgery, due to the involvement of the blood vessels, bleeding is particularly problematic. In cardiac surgery, the multiple vascular anastomoses and cannulation sites, complicated by coagulopathy induced by extracorporeal bypass, can result in bleeding that can only be controlled by topical hemostats. Rapid and effective hemostasis during spinal surgery, where control of osseous, epidural, and/or subdural bleeding or bleeding from the spinal cord is not amenable to sutures or cautery, can minimize the potential for injury to nerve roots and reduce the procedure time. In liver surgery, for example, live donor liver transplant procedures or removal of cancerous tumors, there is a substantial risk of continued bleeding. An effective hemostatic material can significantly enhance patient outcome in such procedures. Even in those situations where bleeding is not massive, an effective hemostatic material can be desirable, for example, in dental procedures such as tooth extractions and other oral surgery, as well as the treatment of abrasions, burns, and the like.

There remains a need for an effective hemostatic product that can be delivered in an easy to use form. Until recently, porous carriers or porous articles, e.g. non-woven fibrous articles containing molecular sieves and hydrophilic oxides had not been disclosed for use as hemostatic devices. Such hemostatic articles comprising molecular sieves have now been found to provide ease of application, effective hemostasis, and reduction in exposure of the patient to high temperature increases owing to high heats of adsorption. These products are also useful in surgical applications that were not available using a powdered molecular sieve or hydrophilic oxide product. The prior art formulations, such as that disclosed in US 2007/0154509, teach the use of two retention aids for reduction of fines loss during the manufacture of the nonwoven materials for use as hemostatic products.

SUMMARY OF THE INVENTION

By using a hemostatic article comprising an adsorbent and a porous carrier, where the carrier is a non-woven fibrous, a sheet or a cast film, the invention addresses virtually all of the shortfalls of the products described above. Modifications in the formulations that are used result in a more effective hemostatic product. In the present invention, all of the ingredients used encourage the progression of the hemostatic mechanism while in prior art formulations the inclusion of certain ingredients had an anticoagulant effect on the clotting time. Certain polyelectrolytes have been found to be effective as retention aids while encouraging a hemostatic response. These include both cationic and anionic polyelectrolytes. Cationic Polyelectrolytes such as cationic polyacrylamides with quarternary ammonium cation groups having charge percent of 15-40% (as a percent of the total monomers that are charged) and molecular weight between 2 and 20 Mg/mol (where Mg is megagrams) are preferred. Also found effective were anionic polyelectrolytes such as anionic polyacrylamide with acrylic acid groups having charge percent of 20-50% and molecular weight between 15 and 40 Mg/mol.

The active ingredient is fully contained in the porous carrier allowing for minimal clean-up to remove the product from the wound.

When the porous carrier is a sheet (and adsorbent) which includes a fibrillated, high surface area fiber and a material that markedly accelerates the contact hemostasis mechanism, the result can be more effective enhancement of coagulation beyond that observed in other products. The adsorbent containing porous sheet that conforms to irregular surfaces can also be readily used in difficult to access wounds and injuries. Other features desirable in a wound dressing such as biocidal activity can be incorporated either directly into the sheet or into a dressing that includes such a sheet.

DETAILED DESCRIPTION OF THE INVENTION

Hemostasis is the arresting of bleeding, whether by normal vasoconstriction, by an abnormal obstruction, by coagulation or surgical means. Hemostasis by coagulation (which is the subject of the products of the present invention) is dependent upon a complex interaction of plasma coagulation and fibrinolytic proteins, platelets, and the blood vasculature. The present invention provides compositions and materials that physically interact with the hemostatic system to treat or prevent bleeding. In particular, the compositions and materials of preferred embodiments result in coagulation of blood.

Effective delivery of hemostatic agents to wounds is particularly desirable in the treatment of injuries characterized by arterial or venous bleeding, as well as in surgical procedures where the control of bleeding can become problematic, e.g., large surface areas, heavy arterial or venous bleeding, oozing wounds, and in organ laceration or resectioning. The compositions and materials of preferred embodiments can possess a number of advantages in delivery of hemostatic agents to wounds, including but not limited to, ease of application and removal, bioadsorption potential, suturability, antigenicity, and tissue reactivity.

Depending upon the nature of the wound and the treatment method employed, the devices of the present invention can employ different forms that can be made through wet laid processing. For example, a puff, ball, fleece, or sponge-shaped form can be preferable for controlling the active bleeding from artery or vein, or for internal bleeding during laparoscopic procedures. In neurosurgery, where oozing brain wounds are commonly encountered, a sheet form of the hemostatic article can be preferred. Likewise, in oncological surgery, especially of the liver, it can be preferred to employ a sheet form or sponge form of the hemostatic article, which is placed in or on the tumor bed to control oozing. In dermatological applications, a sheet form can be preferred. In closing punctures in a blood vessel, a puff form is generally preferred. Despite differences in delivery and handling characteristic of the different forms, the devices are effective in deploying hemostatic agents to an affected site and to rapidly initiate hemostatic plug formation through platelet adhesion, platelet activation, and blood coagulation.

The materials which can be used as the porous carriers for the adsorbent are any article which can support an effective amount of the adsorbent-sheet composite and can be applied to the particular wound being treated. The porous carrier can be composed of natural or synthetic materials and can be woven or non-woven fibrous articles. Adsorbent containing non-woven articles can be prepared by textile-, paper-, extrusion type and a combination or hybrid of processes. The product can be prepared using a variety of fibers including cellulose, aramid, acrylic, polyester, polyolefin, including fibrillated polyethylene and polypropylene, Spectra™ polyethylene (a Honeywell product), chemically modified cellulose fibers such as lyocell and rayon, and synthetic polymers such as Zylon™ (Zylon is also called PBO after its chemical structure, poly(p-phenylene-2,6-benzobisoxazole) and Vectran® (a liquid crystal polymer (LCP)) Various binders can also be used in preparing the sheets, some of which may have functional groups that can aid in the release of coagulation enhancing agents.

The adsorbents which can be used to form the hemostatic article are any of those which are effective in blood clotting. Non-limiting examples of these adsorbents are zeolitic molecular sieves and non-zeolitic molecular sieves. Zeolites are crystalline aluminosilicate compositions which are microporous and which are have a three-dimensional oxide framework formed from corner sharing $AlO_2$ and $SiO_2$ tetrahedra. Both naturally occurring and synthetic zeolites can be used. Non limiting examples of zeolites which can be used are the family of zeolites of structure type X, Y, A, beta, etc. Included in these zeolites are the as synthesized zeolites and those that have been exchanged with other cations, e.g. Ca. Non-zeolite molecular sieves are those which do not contain both $Al_2O_3$ and $SiO_2$ tetrahedra as essential framework constituents, but which exhibit the ion-exchange and/or adsorption characteristics of the zeolites. Other inorganic materials can also be used. Non-limiting examples include montmorillonite and kaolin clays, synthetic and natural porous and non-porous silicas, synthetic and natural silicates, silicate and phosphate glass powders, fibers, or granules, and certain metal oxides such as iron or germanium oxide.

In some embodiments of the present invention, the selected adsorbents have lower heat of adsorption than other adsorbents that may be effective but result in higher heat of adsorption in use. The adsorbents can be loaded into the sheets across a wide range of concentrations spanning 1 wt-% to over 95 wt-%. The size of the fibers and adsorbents used to prepare the sheets can be varied across a wide range starting as low as nanoscale materials to formed beads or crushed extrudate.

Preferably, the fibers employed in the present invention are fibrillated to increase the surface area and the capacity to retain higher loadings of adsorbents and other additives. Suitable fibril-forming thermoplastic polymers may include polymers and copolymers from vinyl chloride, vinyl acetate, acrylonitrile, styrene, butadiene, vinylidene chloride, ethylene and propylene, and condensation polymers, for example polyamide and polyesters, e.g. of glycols and aromatic dicarboxylic acids. Blends of fiber-forming thermoplastic polymer materials may also be used. Natural fibers or fibers chemically derived from natural fibers such as cellulose, rayon and lyocell may also be fibrillated.

A single hemostatic substrate or combination of hemostatic substrate comprising the porous carrier of the present invention can be employed. Different substrate forms can be preferred, for example, puff, fleece, fabric or sheet. In this specification, the term "fleece" is used as a broad term in accordance with its ordinary meaning and includes any fibrous material treated to be flexible, malleable or the like. A fleece may be provided in a non-woven form or in a sheet form. It is to be understood that the fibrous fleece can be treated or coated in any suitable manner to enhance its hemostatic properties. The term "puff" is also used as a broad term in accordance with its ordinary meaning and includes any fibrous material arranged into a soft ball or pad. A puff may be constructed using a sheet. The term "sponge" is also used as a broad term in accordance with its ordinary meaning and includes a material configured to absorb fluids such as blood. A sponge may be constructed using, without limitation, a fleece, puff, fiber, sheet or the like alone or in combination with another material. A homogeneous mixture of different substrate-forming materials can be employed, or composite substrates can be prepared from two or more different formed substrates. In certain embodiments, it can be desirable to add an auxiliary hemostatic agent to the adsorbent hemostatic agents of the present invention. Any suitable hemostatic agent can be deposited upon the substrates of preferred embodiments. Among the hemostatic agents that can be used are bioabsorbable microporous polysaccharide microspheres, clotting factor concentrates, recombinant Factor VIIa (NOVOSEVEN®); alphanate FVIII concentrate; bioclate FVIII concentrate; monoclate-P FVIII concentrate; haemate P FVIII; von Willebrand factor concentrate; helixate FVIII concentrate; hemophil-M FVIII concentrate; humate-P FVIII concentrate; hyate-C® Porcine FVIII concentrate; koate HP FVIII concentrate; kogenate FVIII concentrate; recombinate FVIII concentrate; mononine FIX concentrate; and fibrogammin P FXIII concentrate. Such hemostatic agents can be applied to the substrate in any suitable form (powder, liquid, in pure form, in a suitable excipient, on a suitable support, or the like).

A single hemostatic agent or combination of hemostatic agents can be employed. Preferred loading levels for the hemostatic agent on the substrate can vary, depending upon the nature of the substrate and hemostatic agent, the form of the substrate, and the nature of the wound to be treated.

Hemostatic fabrics can also be prepared from sheets. It is generally preferred that one side of the fabric has a smooth surface and the other side of the fabric has a rough surface. However, in certain embodiments, a fabric having two rough sides can be preferred, such as, for example, for use in connection with an irregular wound, or a deep wound, such as a potentially lethal groin injury. In preferred embodiments, the rough surface is exposed to the wound so as to maximize contact of the fibers with the wound, resulting in an improved hemostatic effect and superior adherence to the wound as well as contact of the adsorbents with the blood flowing from the wound. In preparing a hemostatic fabric comprising fibers loaded with adsorbents, it is generally preferred that the resulting fabric contain from about 1 to about 95 wt-% adsorbents, more preferably from about 5 to about 90 wt-% adsorbents and most preferably from about 50 to about 80 wt-%. In certain embodiments, however, higher or lower levels of adsorbents can be preferred. If an additional hemostatic agent is employed, or other components are to be added to the fibers or other substrate, different loading levels can be preferred.

The hemostatic fabric can be provided in the form of a sheet of a pre-selected size. Alternatively, a larger sheet of hemostatic fabric can be cut, trimmed, or folded to provide a size and shape appropriate to the wound. Alternatively, trimmed sheets can be stacked into multilayers or laminates. Although the hemostatic fabric is biocompatible in cutaneous or topical applications, it can be removed from the wound after a satisfactory degree of hemostasis is achieved, or it can be left in place until the wound is healed. Hemostatic fabric can be useful as artificial skin, and/or can provide antibiotic properties. A hemostatic sponge can be prepared according to methods known in the art for preparing a porous sponge from a biocompatible or bioabsorbable polymeric material. Such methods typically involve preparation of a solution of the polymeric material, crosslinking agents, and foaming agents. The sponge can be loaded with an adsorbent hemostatic agent during formation of the sponge.

While it is generally preferred to apply the hemostatic material directly to the wound, and while the hemostatic material exhibits satisfactory adhesion to many types of wounds, in certain embodiments it can be preferred to incorporate the hemostatic material into a wound dressing including other components such as porous wovens, nonwovens or films.

To ensure that the hemostatic material remains affixed to the wound, a suitable adhesive can be employed, for example, along the edges of one side of the hemostatic structure. Although any adhesive suitable for forming a bond with skin can be used, it is generally preferred to use a pressure sensitive adhesive. Pressure sensitive adhesives are generally defined as adhesives that adhere to a substrate when a light pressure is applied but leave no residue when removed. Pressure sensitive adhesives include, but are not limited to, solvent in solution adhesives, hot melt adhesives, aqueous emulsion adhesives, calenderable adhesive, and radiation curable adhesives. Solution adhesives are preferred for most uses because of their ease of application and versatility. Hot melt adhesives are typically based on resin-tackified block copolymers. Aqueous emulsion adhesives include those prepared using acrylic copolymers, butadiene styrene copolymers, and natural rubber latex. Radiation curable adhesives typically consist of acrylic oligomers and monomers, which cure to form a pressure sensitive adhesive upon exposure to ultraviolet lights.

The most commonly used elastomers in pressure sensitive adhesives include natural rubbers, styrene-butadiene latexes, polyisobutylene, butyl rubbers, acrylics, and silicones. In preferred embodiments, acrylic polymer or silicone based pressure sensitive adhesives are used. Acrylic polymers generally have a low level of allergenicity, are cleanly removable from skin, possess a low odor, and exhibit low rates of mechanical and chemical irritation. Medical grade silicone pressure sensitive adhesives are preferred for their biocompatibility.

Amongst the factors that influence the suitability for a pressure sensitive adhesive for use in wound dressings of preferred embodiments is the absence of skin irritating components, sufficient cohesive strength such that the adhesive can be cleanly removed from the skin, ability to accommodate skin movement without excessive mechanical skin irritation, and good resistance to body fluids. In preferred embodiments, the pressure sensitive adhesive comprises a butyl acrylate. While butyl acrylate pressure sensitive adhesives are generally preferred for many applications, any pressure sensitive adhesive suitable for bonding skin can be used. Such pressure sensitive adhesives are well known in the art.

As discussed above, the hemostatic materials of preferred embodiments generally exhibit good adherence to wounds such that an adhesive, for example, a pressure sensitive adhesive, is not necessary. However, for ease of use and to ensure that the hemostatic material remains in a fixed position after application to the wound, it can be preferable to employ a pressure sensitive adhesive.

While the hemostatic fabrics and other hemostatic materials of preferred embodiments generally exhibit good mechanical strength and wound protection, in certain embodiments it can be preferred to employ a backing or other material on one side of the hemostatic material. For example, a composite including two or more layers can be prepared, wherein one of the layers is the hemostatic material and another layer is, e.g., an elastomeric layer, gauze, vapor-permeable film, waterproof film, a woven or nonwoven fabric, a mesh, or the like. The layers can then be bonded using any suitable method, e.g., adhesives such as pressure sensitive adhesives, hot melt adhesives, curable adhesives, and application of heat or pressure such as in lamination, physical attachment through the use of stitching, studs, other fasteners, or the like.

Advantage can be taken of the surface charge characteristics of the fibers and fillers by ion exchanging additional functional ions such as Ca++ to aid coagulation. Addition of anionic polyelectrolytes may also add ion exchange capacity. The fiber composition and its degree of fibrillation can also be varied to enhance and optimize coagulation. Additional bioactive fillers such as active glasses that release Ca, Ag ions can also be incorporated into the sheets.

One of the more effective embodiments of the present invention involves incorporating 5A zeolite powder and micro-fibrillated aramid fiber into a non-woven sheet prepared using the paper making process technique. The zeolite loading of the sheet is in the range of 65 to 75 wt-%. The sheet is activated at temperature under a nitrogen atmosphere and then stored in a sealed air tight container. Optionally, the sheet can be used in a hydrated form without activation at temperature. The sheet is then removed from the container and applied directly to the wound to stop the bleeding. Once the bleeding has been stopped and the patient stabilized the wound can be further cleaned.

It is believed that the hemostatic devices of the invention do not require an additional hemostatic agent to function effectively to control bleeding, e.g., hemorrhage of a parenchymal organ. As a result, the hemostatic devices of the invention which do not further contain a hemostatic agent have good thermal stability and can be stored for months to a few years without refrigeration and loss of effectiveness. Such embodiments of the invention are useful for various medical situations and are particularly useful for field and emergency use, since each may be stored in a ready-to-use state for a lengthy period, even in the absence of refrigeration. Such devices of the invention also are less expensive to make and/or use compared to hemostatic devices which contain a further hemostatic agent to achieve a comparable level of hemostatic activity. In certain embodiments, the hemostatic devices of the invention further include a therapeutically effective amount of one or more therapeutic agents, such as an agent which promotes wound-healing. Agents which promote wound-healing include anti-inflammatory agents such as agents which inhibit leukocyte migration into the area of surgical injury, anti-histamines; agents which inhibit free radical formation; and bacteriostatic or bacteriocidal agents. In general, a therapeutically effective amount means that amount necessary to delay the onset of, inhibit the progression of, or halt altogether the particular condition being treated. Generally, a therapeutically effective amount will vary with the subject's age, condition, and sex, as well as the nature and extent of the condition in the subject, all of which can be determined by one of ordinary skill in the art. The dosage of therapeutic agent contained in the hemostatic devices of the invention may be adjusted to accommodate the particular subject and condition being treated. As used herein, the phrase, "agents which promote wound-healing" refers to agents, the administration of which, promote the natural healing process of a wound. Agents that promote wound-healing include anti-inflammatory agents, agents which inhibit free radical formation, and bacteriostatic or bacteriocidal agents.

Anti-inflammatory agents are agents which inhibit or prevent an immune response in vivo and include: (i) agents which inhibit leukocyte migration into the area of surgical injury ("leukocyte migration preventing agents"), and antihistamines. Representative leukocyte migration preventing agents include silver sulfadiazine, acetylsalicylic acid, indomethacin, and Nafazatrom. Representative anti-histamines include pyrilamine, chlorpheniramine, tetrahydrozoline, antazoline, and other anti-inflammatories such as cortisone, hydrocortisone, beta-methasone, dexamethasone, fluocortolone, prednisolone, triamcinolone, indomethacin, sulindac, its salts and its corresponding sulfide, and the like.

Representative agents which inhibit free radical formation include antioxidants that inhibit the formation and/or action of oxide products, superoxide dismutase (SOD), catalase, glutathione peroxidase, b-carotene, ascorbic acid, transferrin, ferritin, ceruloplasmin, and desferrioxamine α-tocophenol.

Representative bacteriostatic or bacteriocidal agents include antibacterial substances such as β-lactam antibiotics, such as cefoxitin, n-formamidoyl thienamycin and other thienamycin derivatives, tetracyclines, chloramphenicol, neomycin, gramicidin, bacitracin, sulfonamides; aminoglycoside antibiotics such as gentamycin, kanamycin, amikacin, sisomicin and tobramycin; nalidixic acids and analogs such as norfloxican and the antimicrobial combination of fluoroalanine/pentizidone; nitrofurazones, and the like.

The hemostatic devices of the invention can contain one or more therapeutic agents, alone or in combination with one or more hemostatic agents.

Various additives, optionally, can be incorporated into the hemostatic devices of the invention without substantially reducing the hemostatic activity of these devices. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled within the woven sheets of the present invention, and with each other, in a manner such that there is no interaction which would substantially impair the desired hemostatic activity.

Additives (e.g., retention aids) and binders known in the art of specialty paper making were added together or sequentially to the molecular sieve slurry to improve the retention of the molecular sieve components within the fiber matrix, and to improve paper strength. Such additives include starch, poly-vinyl alcohols (PVA), acrylic emulsions, polyethylene oxides, phenolic resins and microcrystalline cellulose (e.g., carboxymethyl cellulose). The organic additives are added in an amount usually less than 5% by weight of fiber plus molecular sieve on a 200° C. basis. These additives may be added to the makeup tank with the refined fiber and/or added to the head box. The preferred flocculation system contains cationic polyelectrolytes such as cationic polyacrylamides with quaternary ammonium cation groups having charge percent of 15-40% (as a percent of the total monomers that are charged) and molecular weight between 2 and 20 Mg/mol (where Mg is megagrams). Specific cationic polyelectrolytes used in the examples herein were: Percol 292 which has a 21.4% cationic charge and a molecular weight of 5-7 Mg/mol and Percol 175 which has a 21.6% cationic charge and a molecular weight of 9-11 Mg/mol. In addition, anionic polyelectrolytes such as anionic polyacrylamide with acrylic acid groups having charge percent of 20-50% and molecular weight between 15 and 40 Mg/mol can be used. A specific anionic polyacrylamide that is useful in the present invention is Percol E38 which is 30% anionic charge and a molecular weight of 28-30 Mg/mol. All three Percol polyacrylamides are available from Ciba Specialty Chemical Products.

EXAMPLES

Preparation of Hemostatic Paper with a Two Component Retention Aid System:

The following weights are the actual reagent weights (including water):

| | |
|---|---|
| Twaron 1094 (31.4% solids) | 3 g |
| CaA zeolite (82.31% solids) | 4.68 g |
| Alcofix 269 (4% solution) | 0.45 g |
| Percol 38 (0.325% solution) | 1.67 g |

Twaron was disintegrated in a Adirondack Tappi disintegrator 30,000 revs, zeolite added followed by 10,000 revs., Alcofix 269 (poly-DADMAC; poly-diallyldimethylammonium chloride) was added followed by 10,000 revolutions in a 2 liter volume. The 2 liters was diluted to 3 liters and poured into a Techpap retention tester machine. The Percol 38 (anionic polyacryamide, or C-PAM) was added under low shear 200-300 rpm stirring and the sheet was cast on brass forming wire, couched with polyester blotter paper, then dewatered with a roll press. The sheet was dried at ~80° C./30 min. in a sheet drier.

Preparation of Hemostatic Paper with a Single Component Retention Aid System: The following weights are the actual reagent weights (including water) for making an 8" circular handsheet:

| | |
|---|---|
| Twaron 1094 (31.4% solids) | 2.49 g |
| CaA zeolite (82.31% solids) | 3.41 g |
| Percol 292 (0.05% solution) | 11.86 g |

Twaron aramid pulp was disintegrated in a Adirondack Tappi disintegrator for 30,000 revs, then the zeolite was added followed by 10,000 revolutions in a 2 liter volume. The 2 liters was diluted to 3 liters and poured into a Techpap retention tester machine. The Percol 292 (cation polyacryamide, or C-PAM) was added under low shear at 200-300 rpm stirring and the sheet was cast on polyester wire [Albany International JS29 (1442)], couched with polyester blotter paper, then dewatered with a roll press. The sheet was dried at ~80° C./30 min. in a sheet drier.

Preparation of Hemostatic Paper with a Single Component Retention Aid System:

The following weights are the actual reagent weights (including water) for making an 8" circular handsheet:

| | |
|---|---|
| Twaron 1094 (31.4% solids) | 3.12 g |
| CaA zeolite (82.31% solids) | 4.24 g |
| Percol 175 (0.05% solution) | 19.66 g |

Twaron aramid pulp was disintegrated in a Adirondack Tappi disintegrator for 30,000 revs, then the zeolite was added followed by 10,000 revs. in a 2 liter volume. The 2 liters was diluted to 3 liters and poured into a Techpap retention tester machine. The Percol 175 (cation polyacryamide, or C-PAM) was added under low shear at 200-300 rpm stirring and the sheet was cast on polyester wire [Albany International PB577 (1405) triple layer], couched with polyester blotter paper, then dewatered with a roll press. The sheet was dried at ~80° C./30 min. in a sheet drier.

The following protocol was used to test the blood samples.

The apparatus that was used was a TEG® analyzer from Haemoscope Corp. of Morton Grove, Ill. This apparatus measures the time until initial fibrin formation, the kinetics of the initial fibrin clot to reach maximum strength and the ultimate strength and stability of the fibrin clot and therefore its ability to do the work of hemostasis—to mechanically impede hemorrhage without permitting inappropriate thrombosis.

On unactivated samples:
  i. Pipet 360 uL from red topped tube into cup, start TEG test On activated samples:
  i. First, obtain the zeolite-containing paper sample to be tested from lab. They should be weighed, bottled, oven activated (if needed), and capped prior to the start of the experiment. For the following zeolite-containing paper experiments, the paper samples were not activated or oven dried prior to TEG testing. Zeolite-containing paper samples are bottled in twice the amount that need to be tested. For example, if channel 2 is to test 5 mg of zeolite-containing paper and blood, the amount weighed out in the bottle for channel two will be 10 mg. For 10 mg samples, 20 mg is weighed out, etc. See note below for reason.
  ii. For one activated run, three zeolite-containing paper samples were tested at a time. An unactivated blood sample with no additive is run in the first channel. Channels 2, 3 and 4 are blood samples contacted with zeolite-containing paper.
  iii. Once ready to test, set one pipet to 720 uL and other pipet to 360 uL. Prepare three red capped tubes (plain polypropylene-lined tubes without added chemicals) to draw blood and prepare three red additional capped tubes to pour zeolite-containing paper sample into.
  iv. Draw blood from volunteer and bring back to TEG analyzer. Discard the first tube collected to minimize tissue factor contamination of blood samples. Blood samples were contacted with zeolite-containing paper material and running in TEG machine prior to an elapsed time of 4-5 minutes from donor collection.
  v. Open bottle 1 and pour zeolite-containing paper into red capped tube.
  vi. Immediately add 720 uL of blood to zeolite-containing paper in tube.
  vii. Invert 5 times.
  viii. Pipet 360 uL of blood and zeolite-containing paper mixture into cup.
  ix. Start TEG test.

Note: The proportions are doubled for the initial mixing of blood and zeolite-containing paper because some volume of blood is lost to the sides of the vials, and some samples absorb blood. Using double the volume ensures that there is at least 360 uL of blood to pipet into cup. The proportion of zeolite-containing paper to blood that we are looking at is usually 5 mg/360 uL, 10 mg/360 uL, and 30 mg/360 uL The R(min) reported in the Table below is the time from the start of the experiment to the initial formation of the blood clot as reported by the TEG analyzer. The TEG® analyzer has a sample cup that oscillates back and forth constantly at a set speed through an arc of 4° 45'. Each rotation lasts ten seconds. A whole blood sample of 360 ul is placed into the cup, and a stationary pin attached to a torsion wire is immersed into the blood. When the first fibrin forms, it begins to bind the cup and pin, causing the pin to oscillate in phase with the clot. The acceleration of the movement of the pin is a function of the kinetics of clot development. The torque of the rotating cup is transmitted to the immersed pin only after fibrin-platelet bonding has linked the cup and pin together. The strength of these fibrin-platelet bonds affects the magnitude of the pin motion, such that strong clots move the pin directly in phase with the cup motion. Thus, the magnitude of the output is directly related to the strength of the formed clot. As the clot retracts or lyses, these bonds are broken and the transfer of cup motion is diminished. The rotation movement of the pin is converted by a mechanical-electrical transducer to an electrical signal which can be monitored by a computer.

The resulting hemostasis profile is a measure of the time it takes for the first fibrin strand to be formed, the kinetics of clot formation, the strength of the clot (in shear elasticity units of dyn/cm2) and dissolution of clot. The first TEG experiment is with a dilute solution of poly-DADMAC (Alcofix 269) representing the amount of material that would be present in 5, 10 and 30 mg of a finished DADMAC containing paper, as outlined in the first example above, except without the other paper components. The second experiment is the same experiment with a solution of another retention aid, anionic PAM (Percol E38). It is clear from these two experiments that the DADMAC has significant negative effect on the blood coagulation system, similar in action to heparin, while the A-PAM enhances coagulation slightly. The third experiment is a similar TEG run with a solution of cationic PAM, Percol 292, showing a slight enhancement of coagulation. The next two experiments are CaA aramid papers made with Percol 292 and with Percol 175, both showing effective coagulation. The final two experiments are with solutions of cationic PAM Percol 175, showing slight acceleration of clotting. The data therefore show that replacement of the DADMAC/anionic PAM retention aid system with a single component retention aid, cation PAM, gives an effective hemostat without using an additive, such as DADMAC, which could lead to adverse coagulation reactions.

| Full Name | Procedure Name | R(min) |
|---|---|---|
| donor, 23 | Alcofix 269 DADMAC 5 uL of 0.16 wt. % | 50.5 |
| donor, 23 | Alcofix 269 DADMAC 10 uL of 0.16 wt. % | No Clot |
| donor, 23 | Alcofix 269 DADMAC 28 uL of 0.4 wt. % | No Clot |
| donor, 16 | Percol E38 A-PAM 17 uL of 0.0325 wt. % | 22 |
| donor, 16 | Percol E38 A-PAM 35 uL of 0.0325 wt. % | 14.6 |
| donor, 16 | Percol E38 A-PAM 10 uL of 0.325 wt. % | 16.8 |
| donor, 24 | donor 24 native blood | 22.4 |
| donor, 24 | Percol 292 C-PAM 15 uL of 0.05 wt-% | 20.2 |
| donor, 24 | Percol 292 C-PAM 30 uL of 0.05 wt-% | 12.2 |
| donor, 24 | Percol 292 C-PAM 45 uL of 0.1 wt-% | 13.2 |
| donor, 16 | donor 16 native blood | 24.5 |
| donor, 16 | Percol 292 C-Pam-containing Paper 5 mg | 6.2 |
| donor, 16 | Percol 292 C-Pam-containing Paper 10 mg | 5.7 |
| donor, 16 | Percol 292 C-Pam-containing Paper 30 mg | 4.8 |
| donor, 16 | donor 16 native blood | 29.2 |
| donor, 16 | Percol 175 C-Pam-containing Paper 5 mg | 7.2 |
| donor, 16 | Percol 175 C-Pam-containing Paper 10 mg | 6.8 |
| donor, 16 | Percol 175 C-Pam-containing Paper 30 mg | 3.9 |
| donor 3 | Percol 175 C-PAM 45 uL of 0.1 wt-% | 18.2 |
| donor 3 | Percol 175 C-PAM 30 uL of 0.05 wt-% | 17.2 |
| donor 3 | Percol 175 C-PAM 15 uL of 0.05 wt-% | 23.3 |
| donor 3 | donor 3 native sample | 26.4 |
| donor 16 | Percol 175 C-PAM 45 uL of 0.1 wt-% | 26.2 |
| donor 16 | Percol 175 C-PAM 30 uL of 0.05 wt-% | 17.3 |
| donor 16 | Percol 175 C-PAM 15 uL of 0.05 wt-% | 21.8 |
| donor 16 | donor 16 native blood | 31.2 |

The hemostatic articles of the present invention offer a significant hemostatic effect. The incorporation of the adsorbent in a nonwoven sheet form can allow for the use of the product to effectively arrest bleeding during surgical procedures and thereby allow the surgeon to concentrate on the surgery rather than devote significant time to the control of bleeding.

A variety of adsorbents may be used that provide a desired combination of hemostatic effect, lowered heat of adsorption and biocompatibility.

The invention claimed is:

1. A hemostatic article comprising a porous carrier and an adsorbent composition on the porous carrier, said adsorbent composition consisting essentially of:

a) at least one molecular sieve which promotes blood coagulation; and
  b) a blood coagulation enhancing polyelectrolyte, wherein said blood coagulation enhancing polyelectrolyte consists essentially of a cationic polyacrylamide containing quaternary ammonium cation groups, wherein the blood coagulation enhancing polyelectrolyte is present in an amount less than 5% by weight relative to the combined weight of the at least one molecular sieve and the porous carrier.

2. The hemostatic article of claim 1 wherein said blood coagulation enhancing cationic polyacrylamide containing quaternary ammonium cation groups consists of a cationic polyacrylamide having a charge percent of from 15% to 40% and a molecular weight of from 2 Mg/mol to 20 Mg/mol.

3. The hemostatic article of claim 1 wherein the porous carrier is an adsorbent material and wherein said adsorbent composition is incorporated into the porous carrier to thereby avoid direct application of the to a wound.

4. The hemostatic article of claim 1 wherein the porous carrier is a woven fibrous article.

5. The hemostatic article of claim 1 wherein the porous carrier comprises a non-woven fibrous article comprising one or more fibrillated fibers.

6. The hemostatic article of claim 1 wherein said at least one molecular sieve comprises one or more zeolites.

7. The hemostatic article of claim 1 wherein said at least one molecular sieve comprises one or more 5A zeolites, wherein the zeolite comprises from 65 wt. % to 75 wt-% of the hemostatic article, and wherein the porous carrier is a non-woven sheet comprising micro-fibrillated aramid fibers.

8. The hemostatic article of claim 1 wherein said adsorbent composition further includes one or more anti-inflammatory agents, one or more antihistamines, one or more agents which inhibit free radical formation, one or more bacteriostatic or bacteriocidal agents, or a combination thereof.

9. A hemostatic article comprising a fibrous carrier and an adsorbent composition on the fibrous carrier, said adsorbent composition consisting essentially of:

a) at least one molecular sieve or non-zeolite inorganic material which promotes blood coagulation; and
  b) a blood coagulation enhancing polyelectrolyte, wherein said blood coagulation enhancing polyelectrolyte comprises a cationic polyacrylamide having charge percent of 15% to 40% and a molecular weight of from 2 Mg/mol to 20 Mg/mol.

10. The hemostatic article of claim 9 wherein the fibrous carrier comprises a non-woven fibrous article comprising one or more fibrillated fibers.

11. The hemostatic article of claim 9 wherein the fibrous carrier is a woven fibrous article.

12. The hemostatic article of claim 9 wherein the fibrous carrier is porous, wherein the blood coagulation enhancing polyelectrolyte is present in an amount less than 5% by weight relative to the combined weight of the at least one molecular sieve and the fibrous carrier, and wherein the adsorbent composition is incorporated into the fibrous carrier to thereby avoid direct application of the adsorbent to a wound.

13. The hemostatic article of claim 9 wherein said blood coagulation enhancing polyelectrolyte further comprises a combination of said cationic polyacrylamide and an anionic polyacrylamide comprising acrylic acid groups and having a charge percent of 20-50% and molecular weight between 15 and 40 Mg/mol.

14. The hemostatic article of claim 9 wherein the blood coagulation enhancing polyelectrolyte consists of a single polyelectrolyte component which consists of a cationic polyacrylamide.

15. The hemostatic article of claim 9 wherein the molecular sieve is a zeolite.

16. A hemostatic article comprising a fibrous carrier and an adsorbent composition on the fibrous carrier, said adsorbent composition consisting essentially of:
   a) at least one non-zeolite inorganic material which promotes blood coagulation; and
   b) a blood coagulation enhancing polyelectrolyte consisting of a cationic polyacrylamide, an anionic polyacrylamide or a combination thereof.

17. The hemostatic article of claim 16 wherein said wherein said non-zeolite inorganic material comprises natural silicas, synthetic silicas, natural silicates and synthetic silicates, or a combination thereof.

18. The hemostatic article of claim 16 wherein said non-zeolite inorganic material comprise a non-zeolite molecular sieve, silicate glass powder, silicate fibers, silicate granules, a phosphate glass powder, phosphate fibers, phosphate granules, montmorillonite clay, kaolin clay, iron oxide or germanium oxide.

19. The hemostatic article of claim 16 wherein the blood coagulation enhancing polyelectrolyte consists of a single polyelectrolyte component which consists of a cationic polyacrylamide.

20. The hemostatic article of claim 19 wherein said fibrous carrier comprises aramid fibers, acrylic fibers, polyethylene fibers, polypropylene fibers, poly(p-phenylene-2,6-benzobisoxazole) fibers, liquid crystal polymer fibers or acrylonitrile fibers.

21. The hemostatic article of claim 16 wherein said cationic polyacrylamide has a charge percent of 15% to 40% and a molecular weight of from 2 Mg/mol to 20 Mg/mol and said anionic polyacrylamide has a charge percent of from 20% to 50% and a molecular weight of from 15 Mg/mol to 40 Mg/mol.

* * * * *